US010828256B2

(12) United States Patent
Boit et al.

(10) Patent No.: US 10,828,256 B2
(45) Date of Patent: Nov. 10, 2020

(54) MANNITOL GRANULES FOR DIRECT COMPRESSION

(71) Applicant: Roquette Freres, Lestrem (FR)

(72) Inventors: Baptiste Boit, La Gorgue (FR); Philippe Lefevre, Haverskerque (FR)

(73) Assignee: ROQUETT FRERES, Lestrem (FR)

( * ) Notice: Subject to any disclaimer, the term of this patent is extended or adjusted under 35 U.S.C. 154(b) by 476 days.

(21) Appl. No.: 15/745,364

(22) PCT Filed: Jul. 15, 2016

(86) PCT No.: PCT/FR2016/051820
§ 371 (c)(1),
(2) Date: Jan. 16, 2018

(87) PCT Pub. No.: WO2017/013338
PCT Pub. Date: Jan. 26, 2017

(65) Prior Publication Data
US 2020/0085746 A1    Mar. 19, 2020

(30) Foreign Application Priority Data
Jul. 17, 2015   (FR) .................................. 15 56787

(51) Int. Cl.
*A61K 9/16* (2006.01)
*A61K 9/20* (2006.01)

(52) U.S. Cl.
CPC .......... *A61K 9/1623* (2013.01); *A61K 9/1682* (2013.01); *A61K 9/2018* (2013.01); *A61K 9/2095* (2013.01)

(58) Field of Classification Search
CPC .................................................... A61K 9/1623
See application file for complete search history.

(56) References Cited

U.S. PATENT DOCUMENTS

| 4,661,647 | A | 4/1987 | Serpelloni et al. |
| 5,160,680 | A | 11/1992 | Serpelloni et al. |
| 5,573,777 | A | 11/1996 | Serpelloni et al. |
| 6,998,481 | B2 | 2/2006 | Erdmann et al. |
| 9,937,131 | B2 * | 4/2018 | Boit ............... A61K 9/4866 |
| 2003/0118642 | A1 | 6/2003 | Norman et al. |
| 2005/0008693 | A1 * | 1/2005 | Erdmann ............ C07C 29/76 424/464 |
| 2005/0208127 | A1 | 9/2005 | Ogasawara et al. |
| 2011/0135927 | A1 | 6/2011 | Satomi et al. |
| 2012/0053249 | A1 | 3/2012 | Boit et al. |
| 2016/0228370 | A1 * | 8/2016 | Ito ...................... C07C 29/78 |

FOREIGN PATENT DOCUMENTS

| CN | 104721188 A | 6/2015 |
| JP | 2004-175768 A | 6/2004 |
| JP | 2012-180280 A | 9/2012 |
| WO | 2003/103713 A1 | 12/2003 |

\* cited by examiner

*Primary Examiner* — Kyle A Purdy
(74) *Attorney, Agent, or Firm* — Oliff PLC (57) ABSTRACT

The present invention relates to mannitol granules that are of use for the preparation of tablets by direct compression, which do not require a small amount of lubricant in order to be processed. The present invention also relates to a process for preparing such granules. The present invention also encompasses pulverulent compositions comprising these granules, and also direct compression processes using these pulverulent compositions. Finally, the present invention relates to tablets composed of these pulverulent compositions.

13 Claims, 2 Drawing Sheets

FIG. 1

FIG. 2

MANNITOL GRANULES FOR DIRECT COMPRESSION

CROSS REFERENCE TO RELATED APPLICATIONS

This application is a U.S. national stage application of International patent application No. PCT/FR2016/051820, filed Jul. 15, 2016, which claims the priority of French application No. 1556787, filed Jul. 17, 2015, the subject matter of each incorporated in their entirety by reference herein.

A subject of the present invention is mannitol granules that are of use for preparing tablets by direct compression, which require only a small amount of lubricant in order to be processed. A subject of the present invention is also a process for preparing such granules. The present invention also encompasses pulverulent compositions comprising these granules, and also direct compression processes using these pulverulent compositions. Finally, the present invention relates to tablets prepared from these pulverulent compositions, and also to mannitol-based tablets with low lubricant contents.

PRIOR ART

Direct compression techniques make it possible to produce tablets containing precise amounts of active ingredients, at high speed, and at relatively low cost. This technology consists in strongly compressing a pulverulent composition in a matrix by means of a punch, so as to give it the shape of a tablet. It is the high pressure applied which causes aggregation of the powder particles and produces a solid tablet.

These pulverulent compositions typically comprise excipients and active ingredients of interest, for example pharmaceutical, veterinary, cosmetic, food, nutraceutical, chemical or agrochemical interest.

The excipients most commonly encountered in direct compression are diluents, also known as "direct compression excipients", lubricants, (super-)disintegrants, flow agents, pH stabilizers, dyes, flavorings and surfactants.

In order to be capable of forming tablets, the pulverulent composition to be compressed always comprises at least a direct compression excipient and a lubricant.

Direct compression excipients are the major compounds of tablets and are responsible for the tabletability and flow properties of the powder. The most commonly used are microcrystalline cellulose and lactose.

The lubricant itself enables the newly formed tablets to be ejected from the matrices. It limits the stress created by the ejection and thus makes it possible to preserve the integrity of the tablets. The most commonly used is magnesium stearate, followed by calcium stearate and sodium stearyl fumarate.

When the amounts of lubricant used are insufficient, it is no longer possible to obtain satisfactory tablets. This results in particular in the appearance of lamination ("capping") and/or traces of binding.

The lamination is in the form of a horizontal fracturing of the tablets, either in their middle or at the beginning of one of the two curved parts (a phenomenon also known as "capping"). The binding corresponds to the sticking of one part of the material on the matrix, said sticking enduring after ejection of the tablet. Besides the increase in the ejection force measured (which then typically reaches 1000 N), the binding is visible on the tablet: vertical lines are present and correspond to the places where the product remained stuck on the matrix.

A satisfactory tablet must not exhibit traces of binding, and thus has a perfectly smooth edge over its entire circumference. Such a tablet must, moreover, have a surface that is uniform and smooth over its entire surface.

Although they are essential, lubricants have certain drawbacks. One problem frequently encountered with stearate salts is their potential to slow down disintegration and dissolution of the tablets. Another problem lies in the particularly unpleasant taste of these lubricants, and also in their relatively high cost.

In order to overcome this problem, recently, in its patent application US 2012/0053249 A1, the applicant advantageously described a multifunctional excipient capable of performing the role of direct compression excipient, but also of partially performing the role of lubricant. It was a co-agglomerate of mannitol and of granular starch, which made it possible to reduce the amounts of magnesium stearate used.

One disadvantage of these granules lies in the presence of granular starch, which was nevertheless presented as essential in this previous invention. This is because granular starch is easily subject to bacterial contamination, and therefore a strict control of production and storage is required. Moreover, granular starch has a high water content, which can be detrimental to the stability of the active ingredients of the tablets.

On the other hand, mannitol, used alone, could constitute an excellent excipient, in particular for its very substantial chemical inertia with respect to active ingredients, and because of its taste and the low hygroscopicity of its crystalline form.

It would thus be particularly advantageous to be able to dispense with the addition of granular starch in the granules previously developed by the applicant.

The problem, already raised by the applicant in its abovementioned patent application US 2012/0053249 A1, is that the powders obtained using less than 0.5% of granular starch do not have satisfactory flow and tabletability properties.

After numerous studies, the applicant has succeeded in preparing mannitol powders essentially free of granular starch, which not only compress and flow perfectly, but which in addition have lubricating properties.

These powders are non-spherical granules of microcrystalline mannitol, in which the mannitol is both in α crystalline form and in β crystalline form, the α/β ratio being between 10/90 and 90/10, which have a volume mean diameter D4,3 of from 60 to 250 µm, a bulk density of at least 465 g/l, and a specific surface area greater than 0.75 $m^2/g$.

As regards the crystalline form, the literature reports three main forms: α-, β- and δ-mannitols. For applications in direct compression, β-mannitol is conventionally preferred, mainly because of its stability. Moreover, when the mannitol is, in a manner similar to the granules according to the invention, in the form of non-spherical particles of microcrystalline structure, some authors describe the presence of α-mannitol as being harmful. By way of example, patent U.S. Pat. No. 6,998,481 B2 indicates that the presence of α-mannitol is detrimental to the tabletability of the powder.

In the co-agglomerates of mannitol and of granular starch that are described in the abovementioned patent application US 2012/0053249 A1, the mannitol was also partially in the α form. The applicant was therefore already going against a technical preconception by not preferring the purely β form. However, this technical preconception was overcome by means of co-granulation with granular starch. It was therefore not at all obvious that mannitol granules free of granular starch may also be of interest in this double crystalline form.

The applicant has succeeded in developing these granules by virtue of a novel wet granulation process carried out in a multi-stage spray-dryer. This process is in particular carried out in a spray-drying tower in which the angle formed by the wall of the cylindrical upper part and the roof of the chamber is equal to 90°. The relative humidity at the tower outlet is chosen in the range of from 5% to 60%.

Mannitol powders for direct compression have already been described in the prior art. However, none exhibited the combination of features of the granules of the invention.

The powders obtained by melting/extrusion techniques, for example such as those described in patents U.S. Pat. Nos. 4,661,647 A and 5,160,680 A in the name of the applicant, have a specific surface area of less than 0.75 m$^2$/g and a mean diameter generally greater than 300 μm. These powders require larger amounts of lubricant in order to be processed, compared with the granules of the invention.

Single-stage spray-drying processes, for example such as those described in document US 2011/0135927 A1, result in the formation of powders consisting of spherical particles, having a mean diameter of generally less than 60 μm. These powders are not industrially viable, mainly because they do not flow in the presses used in direct compression.

Other documents describe the preparation of non-spherical granules of microcrystalline mannitol, but the crystalline form of which does not correspond to that required by the present invention.

Examples of such documents are:
patent U.S. Pat. No. 6,998,481 B2 (Merck), which relates to mannitol powders for direct compression, in which the mannitol is essentially in β crystalline form;
patent U.S. Pat. No. 5,573,777 A in the name of the applicant which, although silent with regard to the crystalline form of the mannitol, and as emerges from example 1 below, describes powders in which the mannitol is in reality essentially in α crystalline form.

These powders require larger amounts of lubricant in order to be processed, compared with the granules of the invention (see example 1).

AIMS OF THE INVENTION

An objective of the present invention is to provide mannitol granules essentially free of granular starch, which require small amounts of lubricant in order to be processed.

An objective of the present invention is to solve the abovementioned problems by providing a mannitol excipient which has, moreover, the other properties required for a direct compression excipient, in particular in terms of tabletability and flow.

SUMMARY OF THE INVENTION

A first subject of the invention consists of non-spherical granules of microcrystalline mannitol, characterized:
in that said mannitol is both in α crystalline form and in β crystalline form, the α/β ratio being between 10/90 and 90/10; and
in that they are essentially free of granular starch; and
in that they have a volume mean diameter D4,3 of from 60 to 250 μm; and
in that they have a bulk density of at least 465 g/l; and
in that they have a specific surface area greater than 0.75 m$^2$/g.

A second subject of the invention consists of a process for preparing mannitol granules, consisting of:
a step (a) of preparing a mannitol solution;
a step (b) of spray-drying the mannitol solution obtained in step (a) in a multi-stage spray-drying tower (1), comprising the recycling of the fines, characterized:
in that the relative humidity at the tower outlet is chosen in a range of from 5% to 60%; and
in that the multi-stage spray-drying tower (1) comprises a chamber with a conical base (2) consisting of a cylindrical lower part (2a) comprising a static fluidized bed (3), of a conical intermediate part (2b), and of a cylindrical upper part (2c); the angle ($\alpha_{C_y}$) formed by the wall of the cylindrical upper part (2c) and the roof of the chamber (2) being equal to 90°;
a step (c) of recovering the granules thus obtained.

A third subject of the invention consists of a pulverulent composition comprising the mannitol granules according to the invention.

A fourth subject of the invention consists of a process for preparing tablets, consisting of the direct compression of a pulverulent composition according to the invention.

A fifth subject of the invention consists of a tablet consisting of the pulverulent composition according to the invention, or capable of being obtained, or obtained by means of the process for preparing tablets according to the invention.

A sixth subject of the invention consists of a tablet essentially free of granular starch, consisting:
of 30.0% to 100.0% of mannitol;
of less than 0.8% of lubricant;
of 0% to 70.0% of ingredients other than mannitol and lubricant;
the percentages being expressed by dry weight, and their sum being equal to 100%.

A seventh subject of the invention consists of the use of granules in accordance with the invention as direct compression excipient.

DETAILED DESCRIPTION OF THE INVENTION

The granules according to the invention advantageously allow the industrial preparation of tablets of satisfactory appearance and hardness in the presence of very low contents of lubricant.

As a result of this, it is presently possible to produce mannitol-based tablets having low lubricant contents, which have in particular an improved taste compared with the tablets having higher lubricant contents.

The granules of the invention are essentially free of granular starch, and thus make it possible to avoid the disadvantages that can result from its presence.

These granules can be obtained by means of a particular process of spray-drying in a multi-stage spray-drying tower, comprising the recycling of the fines, which is also the subject of the present invention.

In addition to allowing the preparation of granules in accordance with the invention, this process has the advantage of being a continuous process: the spray-dried solution agglomerates a powder of microcrystalline mannitol ("primary powder"), which itself results from the spray-drying of said solution.

The process of the invention allows, moreover, the use of relatively low inlet and outlet temperatures, thereby making it possible to moderate the energy expenditure, while at the same time guaranteeing a process that is industrially relevant, in particular in terms of productivity.

A first subject of the invention consists of non-spherical granules of microcrystalline mannitol, characterized:

in that said mannitol is both in α crystalline form and in β crystalline form, the α/β ratio being between 10/90 and 90/10; and in that they are essentially free of granular starch; and in that they have a volume mean diameter D4,3 of from 60 to 250 µm; and in that they have a bulk density of at least 465 g/l; and in that they have a specific surface area greater than 0.75 m²/g.

The expression "non-spherical granules of microcrystalline mannitol" is such as it is usually understood by those skilled in the art. In particular, under an electron microscope and at a magnification of ×100, these granules generally have variable shapes and an uneven surface. At a magnification of ×1000, fine particles of fine agglomerated crystals are generally visible at their surface. The description "non-spherical" granules typically makes it possible to distinguish them from the particles obtained by single-stage spray-drying of a mannitol solution, which, themselves, are described as "spherical" by those skilled in the art. The term "microcrystalline structure" is intended to mean a structure which, when observed under an electron microscope at a magnification of ×1000, exhibits at the surface only microcrystals and very rarely crystals of larger size. The microcrystal is in particular defined as a crystal of which the sum of the length, the width and the thickness is less than 25 µm. The particles and microcrystals present can have very different shapes, from rounded shapes to elongated shapes. In the granules of the invention, this microstructure is in particular not described as "filamentous". Indeed, even though crystals having needle shapes may be present, they are very greatly in the minority at the surface of the granules. In comparison, patent U.S. Pat. No. 6,998,481 B2 presents a photo of a granule with a texture that is termed filamentous because only needle-shaped microcrystals are visible.

Finally, it is noted that, in the granules of the invention, the microcrystals are not generally oriented.

Under an electron microscope and at a magnification of ×200, these granules are easily distinguished from the conventional crystalline powders of mannitol, composed of well-individualized macrocrystals, that are typically polyhedral, have an even surface, have a substantially constant thickness but a variable length and width, and are generally obtained by simple crystallization from water, from a solution supersaturated with mannitol. They are also distinguished from mannitol powders obtained by agglomeration of a primary powder composed of mannitol macrocrystals. These granules do not have a microcrystalline structure: the crystals, although they are no longer in individualized form, are still clearly visible and appear in the form of sharp edges in these granules. They are also distinguished from the mannitol powders obtained by single-stage spray-drying (not using a fluidized bed) of a mannitol solution, the particles of which, although composed of microcrystalline mannitol, are spherical and have a small diameter, generally between 10 and 50 µm. They are also distinguished from the mannitol powders obtained by melting/extrusion, which are made up of particles which are more compact and more even, which are in the form of more or less angular slabs, and which consist of microcrystals that are generally oriented.

Conventionally, in order for it to be possible for mannitol powders to have the appearance of non-spherical granules of microcrystalline structure, they are prepared by agglomeration of a primary powder composed of particles of microcrystalline structure.

Thus, alternatively, or in a complementary manner, the "non-spherical granules of microcrystalline mannitol" can be defined in that they are obtained, or are capable of being obtained, by agglomeration of a primary powder of mannitol composed of particles of microcrystalline structure, preferentially including the recycling of the fines.

Also, alternatively or in a complementary manner, the granules in accordance with the invention can be defined in that they are not obtained by single-stage spray-drying, by melting/extrusion, or by granulation of macrocrystals.

The granules of the invention are also characterized in that the mannitol is both in α crystalline form and in β crystalline form, the α/β ratio being between 10/90 and 90/10.

The coexistence of the two α and β crystalline forms of mannitol, and also their proportions, can be determined by those skilled in the art by infrared spectrometry or by X-ray diffraction, preferentially by infrared spectrometry. It is for example possible to perform this by carrying out the method as described in example 1 below.

Preferentially, this ratio of α/β crystalline forms is chosen in the range of from 15/85 to 85/15, preferentially from 20/80 to 80/20, preferentially from 25/75 to 75/25, preferentially from 30/70 to 70/30, preferentially from 35/65 to 65/35, preferentially from 40/60 to 60/40, for example from 45/55 to 55/45. It is, for example, equal to 50/50.

The granules of the invention are also characterized in that they are essentially free of granular starch.

The term "essentially free of granular starch" is intended to mean, in the invention, that the granular starch/mannitol dry weight ratio is less than 0.5/99.5, preferentially less than 0.4/99.6, preferentially less than 0.3/99.7, preferentially less than 0.2/99.8, preferentially less than 0.1/99.9, or even preferentially that the granules are totally free of granular starch.

More generally and advantageously, what is explained here applies to starch, regardless of its form, for example to a non-granular starch, which is functionalized (etherification, esterification) or non-functionalized, and hydrolyzed or non-hydrolyzed.

The granules of the invention are also characterized in that they have a volume mean diameter D4,3 of from 60 to 250 µm.

This volume mean diameter D4,3 can in particular be determined by those skilled in the art by means of a dry laser-diffraction particle size analyzer, for example according to the method as described in example 1 below.

The volume mean diameter D4,3 of the granules according to the invention is generally chosen in the range of from 60 to 240 µm, for example from 60 to 220 µm, or even from 60 to 200 µm. This volume mean diameter D4,3 is preferentially greater than 80 µm, preferentially greater than 90 µm, more preferentially greater than 100 µm.

The granules of the invention are also characterized in that they have a bulk density of at least 465 g/l.

The bulk density of the granules according to the invention is generally chosen in the range of from 465 to 600 g/l, for example from 465 to 580 g/l, or even from 465 to 550 g/l. This bulk density is preferentially at least 470 g/l, preferentially at least 480 g/l, preferentially at least 490 g/l, most preferentially at least 500 g/l.

Preferentially, the granules according to the invention have, moreover, a tapped density of at least 470 g/l, preferentially chosen in the range of from 470 to 700 g/l, preferentially from 500 to 650 g/l, most preferentially from 550 to 600 g/l.

This bulk density and this tapped density can be determined by those skilled in the art using the graduated cylinder method, in particular according to the method recommended by the WHO (Document QAS/11.450 FINAL, 2012).

The granules of the invention are also characterized in that they have a specific surface area greater than 0.75 m$^2$/g.

This specific surface area can be determined by those skilled in the art, using the BET method, for example according to the method as described in example 1 below.

The specific surface area of the granules according to the invention is generally between 0.75 and 3.00 m$^2$/g, for example between 0.75 and 2.50 m$^2$/g, or even between 0.75 and 2.00 m$^2$/g, or even between 0.75 and 1.50 m$^2$/g, or even between 0.75 and 1.20 m$^2$/g. This specific surface area is preferentially greater than 0.80 m$^2$/g, preferentially greater than 0.85 m$^2$/g, preferentially greater than 0.90 m$^2$/g, preferentially greater than 0.95 m$^2$/g, more preferentially greater than 1.00 m$^2$/g.

The granules according to the invention can also be characterized in that they are granules for direct compression or "directly compressible" granules. The term "direct compression excipient" is also conventionally used. The granules according to the invention can thus be compressed directly, that is to say without any prior texturing or physical conversion treatment, for instance a prior step of dry or wet granulation.

It is understood by those skilled in the art that this means that they are capable of forming tablets of sufficient hardness, by direct compression, solely in the presence of an effective amount of lubricant. This "effective amount" is such that it effectively allows the formation of tablets, that is to say that, typically, there is an absence of lamination and of binding, and that the ejection force is less than 1000 N, on a production of 10 tablets. This effective amount of lubricant does not generally exceed 3% by dry weight, relative to the total dry weight of the powder to be compressed.

This ability to form satisfactory tablets can in particular be determined by those skilled in the art by direct compression of a pulverulent composition consisting of the excipient to be tested and of lubricant, for example magnesium stearate, using a compression force of 10 kN, in such a way as to form convex tablets with a diameter of 10 mm, a radius of curvature of 9 mm and a weight of 400 mg. The tablets can in particular be formed by means of a rotary press, or by means of a single-punch development press which simulates the compression on an industrial rotary press, for example such as the one used in the examples below. Hardness measurements are carried out on the resulting tablets, by means of a hardness tester, for example such as the one used in example 2 below.

The hardness of the tablets prepared from the excipient to be tested solely in the presence of the lubricant, expressed in Newtons (N), denotes what those skilled in the art commonly refer to as the "tabletability" of the excipient.

The granules according to the invention can thus also be characterized by their tabletability, which is generally between 50 and 500 N, for example between 50 and 400 N, or even between 50 and 300 N, or even between 50 and 200 N, or even between 50 and 150 N. This tabletability is preferentially greater than 70 N, preferentially greater than 80 N, preferentially greater than 90 N, preferentially greater than 100 N.

The granules according to the invention can also be characterized by their flow grade, which is preferentially chosen in the range of from 3 to 15 seconds, preferentially from 4 to 10 seconds, most preferentially from 4 to 8 seconds.

This flow grade can in particular be determined by those skilled in the art according to the method recommended by the European pharmacopoeia, reference "2.9.16. Flowability, 01/2005: 20916; equipment according to figure 2.9.16.-2".

The granules according to the invention can also be characterized by their friability, which is generally between 20% and 50%, for example between 30% and 50%. This friability is preferentially less than 40%, for example between 20% and 40%, for example between 30% and 40%.

In order to measure this friability, those skilled in the art can for example carry out the measurement according to the method as described in example 2 below.

The granules according to the invention are "mannitol granules", but can however comprise other ingredients, in small amounts, as long as this does not infringe the properties sought in the present invention.

Examples of other ingredients are: binders such as polyvinylpyrrolidone (PVP), carboxymethylcellulose (CMC), hydroxypropylmethylcellulose (HPMC), cellulose-based derivatives, acacia gum, gelatin, starch derivatives such as maltodextrins, tragacanth gum; minerals; carbohydrates such as sugars and polyols other than mannitol; food additives, dyes; nutraceutical, pharmaceutical, veterinary or cosmetic active ingredients; preservatives; stabilizers.

Preferentially, the content of other ingredients in the granules, in particular the content of carbohydrates other than mannitol, is less than 15.0%, preferentially less than 10.0%, preferentially less than 5.0%, preferentially less than 2.0%, preferentially less than 1.0%, more preferentially less than 0.5%; these percentages being expressed by dry weight relative to the total dry weight of solids of the granules. Most preferentially, the granules in accordance with the invention are free of other ingredients. In the latter case, this means that the granules consist only of mannitol and of its impurities.

It should be noted in this regard that the mannitol that is of use to the invention preferentially has a richness in mannitol, in particular in D-mannitol, greater than 95.0% by dry weight, preferentially greater than 96.0%, preferentially greater than 97.0%, preferentially greater than 97.5%, preferentially greater than 98.0%, preferentially greater than 98.5%, most preferentially greater than 99.0%.

The other mannitol compounds typically comprise the substances associated with mannitol, in particular sorbitol, maltitol and isomalt, reducing sugars, nickel, heavy metals. Their contents can in particular be determined by those skilled in the art according to the methods recommended by the European pharmacopoeia, in particular taken from the reference document "Mannitol, 01/2014:0559".

In particular, the mannitol that is of use in the invention preferentially has a reducing sugar content not exceeding 0.1%, a nickel content not exceeding 1 ppm and a heavy metal content not exceeding 5 ppm.

The granules according to the invention can also be characterized by their loss of weight on drying, which is preferentially between 0.00% and 0.50% by weight. This loss of weight on drying is preferentially less than 0.40% by weight, preferentially less than 0.30%, preferentially less than 0.25%, more preferentially than 0.20%, for example between 0.01% and 0.20%, or even between 0.02% and 0.15%.

This loss of weight on drying can in particular be determined by those skilled in the art according to the method recommended by the European pharmacopoeia, reference "2.2.32. Loss on drying, 07/2015: 20232".

A subject of the present invention is also a process for preparing mannitol granules, particularly of use for the preparation of granules in accordance with the invention, which consists of:
  a step (a) of preparing a mannitol solution;
  a step (b) of spray-drying the mannitol solution obtained in step (a) in a multi-stage spray-drying tower (1), comprising the recycling of the fines, characterized:
    in that the relative humidity at the tower outlet is chosen in a range of from 5% to 60%;
    and in that the multi-stage spray-drying tower (1) comprises a chamber (2) consisting of a cylindrical lower part (2a) comprising a static fluidized bed (3), of a frustoconical intermediate part (2b), and of a cylindrical upper part (2c); the angle ($\alpha_{Cy}$) formed by the side wall of the cylindrical upper part (2c) and the roof of the chamber (2) being equal to 90°;
  a step (c) of recovering the granules thus obtained.

Preferentially, the mannitol solution prepared in step (a) has a solids content by weight of between 20% and 60%, preferentially between 30% and 50%, preferentially between 35% and 45%, for example equal to 40%.

Preferentially, this solution is maintained at a temperature such that it makes it possible to keep the mannitol in the dissolved state or in the form of microcrystals.

Preferentially, the relative humidity to which step (b) refers is chosen in a range of from 5% to 50%, preferentially from 10% to 40%, preferentially from 10% to 30%, preferentially from 15% to 25%.

Preferentially, the surface of the roof of the chamber (2) of the spray-drying tower (1) referred to in step (b) is essentially flat, preferentially totally flat.

Preferentially, the chamber (2) of the spray-drying tower (1) has a volume of from 8 to 1500 m$^3$, preferentially from 10 to 1000 m$^3$, preferentially from 50 to 800 m$^3$, preferentially from 100 to 700 m$^3$, preferentially from 200 to 600 m$^3$, preferentially from 300 to 500 m$^3$. This volume is, for example, equal to 400 m$^3$.

Preferentially, the dimensions of the spray-drying tower (1) are such that the diameter $D_T$ is chosen in the range of from 2.0 to 16.0 m, preferentially from 5.0 to 15.0 m, preferentially from 8.0 to 12.0 m; the $H_T/D_T$ ratio is chosen in the range of from 0.9 to 1.6, preferentially from 0.9 to 1.4, preferentially from 1.0 to 1.2; the $D_T/D_L$ ratio is chosen in the range of from 3.5 to 4.5; the $H_{Co}/H_{Cy}$ ratio is chosen in the range from 4.0 to 9.0, preferentially from 6.0 to 9.0, preferentially from 8.0 to 9.0; the $H_{Co}/H_L$ ratio is chosen in the range of from 5.0 to 25.0, preferentially from 10.0 to 25.0, preferentially from 15.0 to 21.0; and the cone angle $\alpha_{Co}$ is chosen in the range of from 18.0 to 25.0°, preferentially from 20.0 to 24.0°, preferentially from 22.0 to 23.0°.

For example, the dimensions of the spray-drying tower (1) are such that the diameter $D_T$ is equal to 10.0 m; and/or the $H_T/D_T$ ratio is equal to 1.1; and/or the $D_T/D_L$ ratio is equal to 4.0; and/or the $H_{Co}/H_{Cy}$ ratio is equal to 8.3; and/or the $H_{Co}/H_L$ ratio is equal to 18.2; and/or the cone angle $\alpha_{Co}$ is equal to 22.4°.

Preferentially, the flow rate is chosen such that the speed of the air of the static fluidized bed is from 0.3 to 1.5 m/s.

For the recycling of the fines, the fines and the air are preferentially extracted at the roof of the chamber (2) of the spray-drying tower (1), and the fines are preferentially recycled at the bottom of the tower, i.e. in the lower portion of the intermediate part (2b) of the chamber (2).

The extraction of the fines can advantageously be carried out by means of two drying chamber exhausts (4a and 4b), which are advantageously opposite relative to the vertical axis of the spray-drying tower (1). Their edge is advantageously located at at least 1 m from the wall of the cylindrical part (2c).

Advantageously, the fines and the air that are extracted from the chamber of the tower are separated by means of at least one cyclone, preferentially two cyclones in series.

The spray nozzle pressure is preferentially chosen in the range of from 30 to 300 bar, preferentially from 150 to 250 bar, for a solution flow rate ranging from 1000 to 7000 kg/h, preferentially from 3000 to 5000 kg/h, for example from 400 to 4200 kg/h.

Preferentially, the temperature of the inlet air upstream of the top of the tower ("inlet temperature") is chosen in the range of from 120 to 240° C., preferentially from 170 to 210° C. This temperature is for example equal to 190° C.

Preferentially, the temperature of the tower outlet air ("outlet temperature") is between 50 and 120° C., preferentially between 50 and 100° C., preferentially between 50 and 90° C. This outlet temperature is preferentially chosen in the range of from 60 to 80° C.

Preferentially, the temperature of the air of the static fluidized bed (3) is chosen in the range of from 50 to 120° C., preferentially from 90 to 120° C. This temperature is for example equal to 110° C.

Preferentially, the process according to the invention also comprises a step (b'), prior to step (c), of cooling the newly formed granules, preferentially by means of passing them over a vibrated fluidized bed, at a temperature preferentially between 15 and 25° C., for example at a temperature of 20° C.

In the case where the granules of the invention comprise ingredients other than mannitol, the process according to the invention includes the use of these other ingredients, which can be introduced in dry form into the spray-drying chamber, for example via the system for recycling the fines or an additional inlet, and/or in the form of a suspension and/or a solution, for example via the pulverized mannitol solution.

The subject of the present invention is also a pulverulent composition, in particular a pulverulent composition for direct compression, comprising the mannitol granules according to the invention.

This pulverulent composition preferentially consists of:
  30.0% to 100% of mannitol granules according to the invention;
  0.0% to 70.0% of ingredients other than the mannitol granules according to the invention; the percentages being expressed by dry weight, and their sum being equal to 100%.

Examples of other ingredients are typically:
  direct compression excipients or diluents other than the mannitol of the invention, for example (i) directly compressible polyols, such as the directly compressible forms of sorbitol, maltitol, xylitol, isomalt, lactitol or erythritol, or of mannitol other than that according to the invention, (ii) directly compressible sugars, such as the directly compressible forms of sucrose, dextrose, dextrates, lactose or allulose, (iii) microcrystalline cellulose, and (iv) directly compressible minerals;
  lubricants;
  dispersants or disintegrants, such as sodium starch glycolate, crosslinked carboxymethylcellulose, crosslinked polyvinylpyrrolidone, or starches;

granulation agents, such as polyvinylpyrrolidone, acacia gum, dextrose, gelatin, maltodextrins, starches, starch derivatives, or tragacanth gum; food additives, such as flavorings or acidifying agents;

dyes, such as mineral dyes, pigments or soluble dyes;

glidants (for example silica dioxide), or anti-sticking agents (for example talc);

active ingredients, in particular pharmaceutical, veterinary, nutraceutical or cosmetic active ingredients.

Preferentially, the pulverulent composition for direct compression in accordance with the invention has a content of mannitol granules according to the invention of at least 40.0%, preferentially at least 50.0%, preferentially at least 60.0%, preferentially at least 70.0%, preferentially at least 80.0%, preferentially at least 90.0%; these percentages being expressed by dry weight of granules in accordance with the invention relative to the total dry weight of the pulverulent composition. This mannitol granule content is generally less than 100.0%. It is typically chosen in the range of from 90.0% to 99.0%, or even from 95.0% to 99.0%.

Preferentially, the composition according to the invention has a lubricant content of from 0.1% to 3.0%, generally from 0.2% to 3.0%, or even from 0.3% to 3.0%, or even from 0.4% to 3.0%, or even from 0.5% to 3.0%, or even from 0.6% to 3.0%; these percentages being expressed by dry weight of lubricants relative to the total dry weight of the pulverulent composition. Preferentially, this lubricant content is less than 2.5%, preferentially less than 2.0%, preferentially less than 1.5%, preferentially less than 1.0%. It is for example chosen in the range of from 0.6% to 0.9%, or even from 0.6% to 0.8%, or even from 0.6% to 0.7%.

Preferentially, the lubricants of the invention comprise magnesium stearate, at a content preferentially greater than 30.0%, preferentially greater than 50.0%, preferentially greater than 90.0%; these percentages being expressed by dry weight of magnesium stearate relative to the total dry weight of the lubricants. Most preferentially, the lubricant of the invention consists entirely of magnesium stearate.

Preferentially, in the pulverulent composition in accordance with the invention, the mannitol granules according to the invention represent at least 50.0% of the direct compression excipients, preferentially at least 60.0%, preferentially at least 70.0%, preferentially at least 80.0%, preferentially at least 90.0%, preferentially at least 95.0%, preferentially at least 98.0%, preferentially at least 99.0%; these percentages being expressed by dry weight of granules in accordance with the invention relative to the total dry weight of compression excipients of the pulverulent composition. Most preferentially, the pulverulent composition is free of direct compression excipients other than the mannitol granules in accordance with the invention.

A subject of the present invention is also a process for preparing tablets, preferentially for reducing the amounts of lubricant in these tablets, consisting of the direct compression of a pulverulent composition according to the invention, preferentially by means of a rotary press.

A subject of the present invention is also a tablet composed of the pulverulent composition in accordance with the invention, or capable of being obtained by, or obtained by means of the process for preparing tablets by direct compression according to the invention.

For the purposes of the present invention, the term "tablet" is intended to mean a solid preparation obtained by direct compression of a pulverulent composition. The tablet can for example be for food, pharmaceutical, cosmetic or nutraceutical purposes. The tablets may be tablets to be sucked, to be chewed or to be swallowed, or orodispersible tablets, or effervescent tablets. These tablets may be intended for human beings, who may be adults or children, or for animals. They may also be tablets for chemical or agrochemical purposes. These tablets may be single-layer or multilayer tablets. In the present invention, the tablets are preferentially convex in shape.

A subject of the present invention is also a tablet essentially free of granular starch, consisting:

of 30.0% to 100.0% of mannitol;

of less than 0.8% of lubricant;

of 0% to 70.0% of ingredients other than mannitol and lubricant;

the percentages being expressed by dry weight, and their sum being equal to 100%.

Preferentially, the tablet according to the invention has a mannitol content of at least 40.0%, preferentially at least 50.0%, preferentially at least 60.0%, preferentially at least 70.0%, preferentially at least 80.0%, preferentially at least 90.0%; these percentages being expressed by dry weight of mannitol relative to the total dry weight of the tablet. This mannitol content is generally less than 100.0%. It is typically chosen in the range of from 90.0% to 99.0%, or even from 95.0% to 99.0%.

Preferentially, the tablet according to the invention has a lubricant content of from 0.1% to 3.0%, generally from 0.2% to 3.0%, or even from 0.3% to 3.0%, or even from 0.4% to 3.0%, or even from 0.5% to 3.0%, or even from 0.6% to 3.0%; these percentages being expressed by dry weight of lubricants relative to the total dry weight of the tablet. Preferentially, this lubricant content is less than 2.5%, preferentially less than 2.0%, preferentially less than 1.5%, preferentially less than 1.0%. It is for example chosen in the range of from 0.6% to 0.9%, or even from 0.6% to 0.8%, or even from 0.6% to 0.7%.

Preferentially, the mannitol of the tablets is both in $\alpha$ crystalline form and in $\beta$ crystalline form, the $\alpha/\beta$ ratio being in particular as defined above.

A subject of the present invention is also the use of the granules in accordance with the invention as direct compression excipient.

Preferentially, the granules in accordance with the invention are also used to reduce the amounts of lubricant in a pulverulent composition for direct compression.

It should be noted that, in the present invention, it is understood that the expression "between X and Y" covers a range of values excluding the limits mentioned, whereas the expression "in the range of from X to Y" or alternatively "from X to Y" covers a range of values including the limits mentioned.

Figure 1:
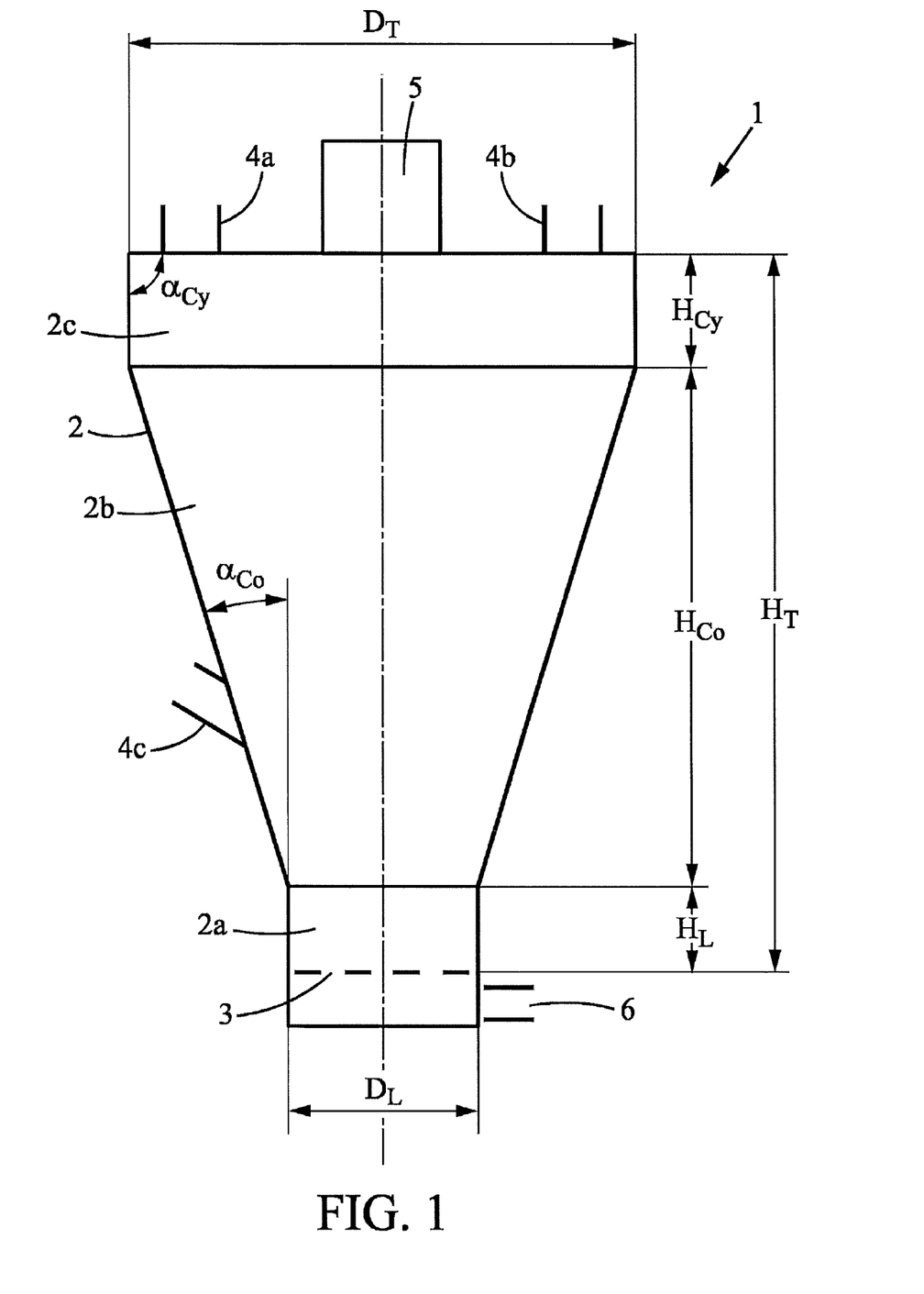

FIG. 1 is a diagrammatic representation of a multi-stage spray-drying tower, comprising a device for the recycling of the fines, that is of use in the invention. The spray-drying tower 1 comprises a chamber 2 of height $H_T$ consisting of a cylindrical lower part 2a of height $H_L$, comprising a static fluidized bed 3, of a frustoconical intermediate part 2b of height $H_{Co}$, of smallest diameter DL, of largest diameter $D_T$ and of cone angle $\alpha_{Ce}$, and of a cylindrical upper part 2c of height $H_{Cy}$ and of diameter $D_T$. The angle $\alpha_{Cy}$ formed by the side wall of the cylindrical upper part 2c and the roof of the chamber 2 is equal to 90°. For the recycling of the fines, the spray-drying tower comprises two opposite extraction drying chamber exhausts 4a and 4b located at the roof of the chamber 2 and an inlet 4c for the fines, located in the lower portion of the frustoconical intermediate part 2b of the chamber 2. The tower includes a device 5 which comprises a spraying system and an air disperser. The tower includes an air inlet 6 which feeds the static fluidized bed 3.

Figure 2:
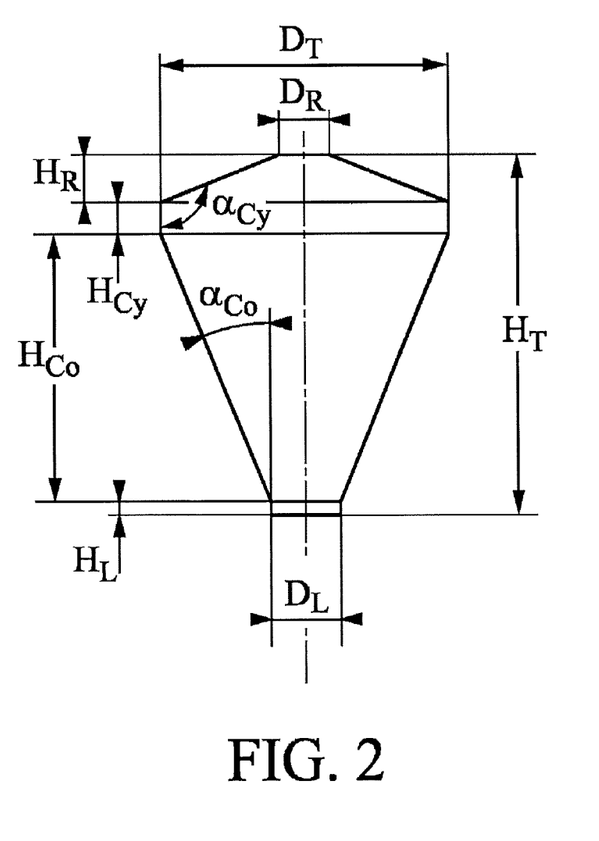

FIG. 2 is a diagrammatic representation of a chamber for a multi-stage spray-drying tower comprising a device for the recycling the fines, comprising the same features as the chamber 2 of the example of FIG. 1 with the exception of the following features: the angle $\alpha_{Cy}$ formed by the side wall of the cylindrical upper part and the roof of the chamber is equal to 110°, as for the MSD 20 spray dryer (NIRO) used in the abovementioned patent application US 2012/0053249 A1.

The invention will be understood more clearly from the following examples which are intended to be illustrative and nonlimiting.

EXAMPLES

Mannitol-Based Excipients Tested

Several powders of granulated mannitol were prepared by spray-drying a solution of mannitol at 40% solids in a multi-stage spray-drying tower (of the MSD, NIRO type) comprising the recycling of the fines at the bottom of the tower. The upstream air flow rate was 34 000 Nm³/h, and the static fluidized bed air flow rate was 15 000 Nm³/h. The static fluidized bed air temperature was 110° C. The flow rate of the spray-dried solution was approximately 4200 kg/h. To spray-dry the solution, two high-pressure 645×32 nozzles (Spraying System SB) were used.

In order to produce the mannitol granules IN-1, IN-2, and CP-1 to CP-4, a spray-drying tower in accordance with the invention, having a chamber 2 as represented in FIG. 1, i.e. having the following dimensions, was used:

$H_T$=10.7 m
$H_{Cy}$=1.1 m
$H_{Co}$=9.1 m
$H_L$=0.5 m
$D_T$=10 m
$D_L$=2.5 m
$\alpha_{Cy}$=90°
$\alpha_{Co}$=22.4°
volume=400 m³.

In order to produce the mannitol granules CP-5 and CP-6, a spray-drying tower having a chamber as represented in FIG. 2, i.e. having an angle $\alpha_{Cy}$ of 110°, was used. This spray-drying chamber corresponds to that used in the abovementioned patent application US 2012/0053249 A1. The dimensions of this chamber are the following:

$H_T$=12.3 m
$H_{Cy}$=1.1 m
$H_{Co}$=9.1 m
$H_L$=0.5 m
$D_T$=10 m
$D_L$=2.5 m
$D_R$=1.7 m
$H_R$=1.6 m
$\alpha_{Cy}$=110°
$\alpha_{Co}$=22.4°
volume=450 m³.

The outlet temperatures; the inlet temperatures and the relative humidities at outlet that were used are indicated in table 1.

The granules AA-1 correspond to the product Parteck® M200 (Merck), described in patent U.S. Pat. No. 6,998,481 B2.

The granules AA-2 correspond to the product Pearlitol® 400DC (Roquette Frères), described in patent U.S. Pat. No. 5,160,680 A.

The granules AA-3 correspond to the product Pearlitol® 200SD (Roquette Frères), described in patent U.S. Pat. No. 5,573,777 A in example 1.

The granules AA-4 correspond to the product Mannogem® EZ (SPI Pharma).

Direct Compression

In the examples which follow, the powders were compressed using a compression force of 10 kN, so as to form convex tablets having a diameter of 10 mm with a radius of curvature of 9 mm, and a weight of 400 mg.

The press used was a single-punch development press which simulates the compression on an industrial rotary press (Stylcam® 200R, Medel'Pharm), controlled by means of the Analis software, using the Stylcam® standard profile. This press advantageously makes it possible to simulate the operation of industrial rotary presses. The press was adjusted to a speed of 10 tablets per minute.

Before the compression step, the powders were intimately mixed with the lubricant. This mixing was carried out more precisely by placing the powder and the lubricant in a sealed container having a volume of between 2 and 3 times the volume of powder to be tested. This container was then fixed in an epicycloidal mixer (Turbula T2C, Willy A. Bachofen AG Maschinenfabrik, CH-4005 Basel) adjusted to approximately 49 rotations per minute, and said mixer was rotated for 5 minutes.

Example 1

Evaluation of the Minimum Amounts of Lubricants Required to Compress Various Mannitol Excipients In this example, the minimum amounts of lubricants required to compress the various mannitol excipients were determined.

The lubricant used was magnesium stearate (Bärlocher plant magnesium stearate, Wiga Pharma GmbH).

The powders were moreover characterized from the point of view of their crystalline polymorphism (α/β crystalline form ratio), of their volume mean diameter D4,3, of their bulk density and of their specific surface area.

The results obtained are given in Table 1. In order to facilitate reading, the 1st column indicates whether the granules are intended to illustrate the invention ("IN-X"), whether they are comparative granules ("CP-X"), or whether they are granules illustrating the prior art ("AA-X").

Determination of the bulk density. The bulk densities of the excipients to be tested were measured according to the method recommended by the WHO (Document QAS/11.450 FINAL, 2012).

2. Determination of the specific surface area. The specific surface areas of the excipients to be tested were determined by means of a specific surface area analyzer (SA3100-type Beckman-Coulter) based on a test for absorption of nitrogen onto the surface of the product subjected to the analysis, by following the technique described in the article BET Surface Area by Nitrogen Absorption by S. Brunauer et al. (Journal of American Chemical Society, 60, 309, 1938). The BET analysis was carried out in 3 points.

3. Determination of the α/β ratio. The ratio of α/β crystalline forms was determined by Fourier transform infrared spectrometry, using the potassium bromide pellet method.

The samples were analyzed by the potassium bromide pellet technique on a spectrometer (Nexus™ FT-IR, Nicolet), equipped with the OMNIC software (Thermo Electron Corporation). The calibration and the quantification were carried out by means of the TQ-Analyst software (Thermo Electron Corporation), using the spectral regions (3050-2850 cm$^{-1}$) recorded with a scan number of 20 and a resolution of 4 cm$^{-1}$.

The calibration was carried out by means of the α and β forms identified as such by virtue of the description given by L. Walter-Levy (Walter-Levy L. (23/12/1968). *Cristallochimie. Sur les variétés cristallines du D-mannitol [Regarding the crystal varieties of D-mannitol]*. C.R. Acad. Sc., Paris, t. 267, Series C, 1779-82), and of five physical mixtures of these two forms, covering the range (85, 65, 50, 35, and 15%). These mixtures, and the pure forms, were ground in an agate mortar before analysis. The quantification was obtained using the preceding calibration.

4. Determination of the mean diameter. The mean diameter of the excipients to be tested was measured by laser diffraction, by means of an LS 13-320 device (Beckman-Coulter), equipped with its powder dispersion module (dry process), according to the technical manual and the specifications of the manufacturer. The operating conditions of hopper screw speed and of vibration intensity of the dispersion chute were determined in such a way that the optical concentration is between 4% and 12%, ideally it is 8%. The measuring range of the diffraction particle size analyzer was from 0.04 μm to 2000 μm. The results were calculated as % by volume, and expressed in μm. The value of the volume mean diameter (arithmetic mean) D4,3 was determined from the particle size distribution curve.

5. Determination of the minimum amount of lubricant required to prepare tablets. In order to determine the minimum amount of lubricant required to prepare tablets, pulverulent compositions using increasing amounts of lubricant were compressed by direct compression, as indicated in point 2 in the introduction to the examples. For each test, 10 tablets were prepared. The minimum amount of lubricant is that for which: (i) no binding nor any lamination is apparent, and (ii) the ejection force measured is less than 1000 N.

The results obtained are given in Table 1.

patent application US 2012/0053249 A1 does not make it possible to obtain granules which have the combination of characteristics of the granules of the invention, and therefore to solve the technical problem of the invention.

The granules of the invention IN-1 and IN-2 require low amounts of lubricant, and thus enable the lubricant contents to be reduced in the tablets, which then in particular have an improved taste.

Example 2

Characteristics of Granules According to the Invention

In this example, other characteristics of the granules IN-1 and IN-2 in accordance with the invention were determined. The results obtained are given in Table 2.

1. Determination of the tabletability. Pulverulent compositions consisting of the granules IN-1 or IN-2 and of magnesium stearate (Bärlocher plant magnesium stearate, Wiga Pharma GmbH) were compressed by direct compression. The hardness of the tablets was measured using a hardness tester (Schleuniger Pharmatron 8M). This hardness corresponds to the tabletability of the excipient.

2. Determination of the flow grade. The flow grade was determined according to the method recommended by the European pharmacopoeia, reference "2.9.16. Flowability, 01/2005: 20916; equipment according to figure 2.9.16.-2".

3. Determination of the friability. A powder of granules in accordance with the invention was subjected to a mechanical action in a friability tester (Erweka TAR 220, Erweka, 63150, Heusenstamm) equipped with an abrasion drum (chosen from the Erweka document references: ref 11-3x5-3xxx or ref 11-3x5-x3xx or ref 11-3x5-4xxx or ref 11-3x5-x4xx), which rotates at a uniform rotation speed of 25 rpm, into which 5 identical steel balls, 17 mm in diameter and

TABLE 1

| | Process | | | | | Granule characteristics | | | |
| --- | --- | --- | --- | --- | --- | --- | --- | --- | --- |
| Ref | Inlet temperature | Outlet temperature | Relative humidity | $\alpha_{C_y}$ | α/β Ratio | Bulk density | Vol. Mean Diam. D4,3 | Specific surface area | Lubrication min % of lubricant |
| IN-1 | 190° C. | 69° C. | 20.3% | 90° | 50/50 | 510 g/l | 163 μm | 1.10 m²/g | 0.6% |
| IN-2 | 190° C. | 71° C. | 18.9% | 90° | 50/50 | 517 g/l | 172 μm | 1.25 m²/g | 0.6% |
| CP-1 | 140° C. | 48° C. | 55.0% | 110° | 55/45 | 403 g/l | 168 μm | 2.15 m²/g | 1.0% |
| CP-2 | 160° C. | 52° C. | 45.2% | 110° | 60/40 | 426 g/l | 175 μm | 2.10 m²/g | 1.0% |
| CP-3 | 180° C. | 62° C. | 28.2% | 110° | 60/40 | 444 g/l | 155 μm | 2.00 m²/g | 1.0% |
| CP-4 | 220° C. | 79.5° C. | 13.3% | 110° | 60/40 | 465 g/l | 151 μm | 0.75 m²/g | 1.0% |
| CP-5 | 310° C. | 125° C. | 2.6% | 90° | 90/10 | 500 g/l | 172 μm | 0.20 m²/g | 2.5% |
| CP-6 | 130° C. | 44.8° C. | 62.5% | 90° | 40/60 | 438 g/l | 221 μm | 2.00 m²/g | 1.5% |
| AA-1 | Process according to patent U.S. 6,998,481 B2 | | | | <10/90 | 559 g/l | 197 μm | 3.60 m²/g | 1.2% |
| AA-2 | Process according to patent U.S. 5,160,680 A | | | | 15/90 | 682 g/l | 449 μm | 0.40 m²/g | 0.8% |
| AA-3 | Process according to patent U.S. 5,573,777 A | | | | >90/10 | 509 g/l | 157 μm | 0.45 m²/g | 2.0% |
| AA-4 | / | | | | >90/10 | 450 g/l | 120 μm | 1.20 m²/g | 2.0% |

The comparative granules CP-1 to CP-6 and the prior art granules AA-1 to AA-4 require amounts of lubricants of from 0.8% to 2.5% for the production of tablets. These granules in fact have an insufficient bulk density and/or an insufficient specific surface area, and/or a crystalline form which is not in accordance with the invention.

The results obtained with the granules CP-1 to CP-4 make it possible in particular to show that the simple removal of the starch in the processes used in the abovementioned weighing 18.87 g, were introduced. 15 g of the powder having a particle size of between 100 and 200 μm were introduced into the crushing chamber. The device was rotated for 15 minutes. The weight proportion represented by the residue retained on a sieve having a mesh width of 100 μm was determined. The friability value corresponds to the percentage of powder not retained by the sieve. The higher the percentage of powder not retained by the abovementioned sieve, the greater the friability.

4. Determination of the loss of weight on drying. The loss of weight on drying was determined according to the method recommended by the European pharmacopoeia, reference "2.2.32. Loss on drying, 07/2015: 20232".

5. Determination of the richness in D-mannitol. The richness in D-mannitol was determined according to the method recommended by the European pharmacopoeia in reference document "Mannitol, 01/2014:0559".

6. Determination of the tapped density. The tapped density was measured according to the method recommended by the WHO (Document QAS/11.450 FINAL, 2012).

TABLE 2

| Granules | IN-1 | IN-2 |
|---|---|---|
| Tabletability | 107 N | 112 N |
| Flow grade | 5 seconds | 6 seconds |
| Friability | 37.6% | 39.6% |
| Loss of weight on drying | 0.07% | 0.10% |
| Richness in D-mannitol | 98.5% | 98.9% |
| Tapped density | 560 g/l | 575 g/l |

The granules according to the invention have the qualities required for a compression excipient intended for an industrial production of tablets. They allow correct filling of the matrices, i.e. uniform and reproducible filling with a precise amount of powder, and flow correctly in the equipment used in direct compression. They are chemically and physically stable. They are sufficiently cohesive to allow them to be transported or to allow mixtures to be prepared. They do not hinder the bioavailability of the other ingredients of the powder and make it possible to obtain tablets which dissolve correctly, in particular on contact with water. They allow homogeneous mixing of the ingredients of the composition, and have a good absorption capacity. They allow the production of tablets with an acceptable texture and an acceptable taste, which are required when the tablet is intended to be ingested. They generate packaging and transportation costs which adhere to commercial standards, that is to say that there is a good ratio between the weight of powder transported and the volume required for packaging this weight.

The invention claimed is:

1. Non-spherical granules of microcrystalline mannitol, comprising:
mannitol is both in α crystalline form and in β crystalline form, with a α/β ratio between 10/90 and 90/10; wherein said non-spherical granules of microcrystalline mannitol
are essentially free of granular starch;
have a volume mean diameter D4,3 of from 60 to 250 μm; and
have a bulk density of at least 465 g/l; and
have a specific surface area greater than 0.75 m$^2$/g.

2. The granules according to claim 1, wherein the α/β ratio is from 15/85 to 85/15.

3. The granules according to claim 1, wherein the volume mean diameter D4,3 is greater than 80 μm.

4. The granules according to claim 1 the bulk density is at least 470 g/l.

5. The granules according to claim 1, the specific surface area is greater than 0.80 m$^2$/g.

6. The granules according to claim 1, wherein the granules have a tabletability of between 50 and 500 N.

7. The granules according to claim 1, wherein the granules have a flow grade of from 3 to 15 seconds.

8. A process for preparing mannitol granules with α crystalline and β crystalline forms, consisting of:
preparing a mannitol solution;
feeding the solution to a multistage spray-dryer tower comprising of a cylindrical lower part defining a static fluidized bed and inlet, a frustoconical chamber, and a cylindrical upper part with a roof comprising a feed inlet and tower outlets through which fines are removed, recycling the fines to the tower; and recovering the granules,
wherein the relative humidity at the tower outlet is chosen in a range of from 5% to 60%; and
wherein a cylindrical wall of the lower part forms an angle of $\alpha_{Cy}$ with a wall of the frustoconical chamber, which is arranged at an angle of ($\alpha_{Cy}$) relative to a side wall of the cylindrical upper part and the roof of the chamber, and $\alpha_{Cy}$ is equal to 90°.

9. A pulverulent composition comprising the granules according to claim 1.

10. A process for preparing tablets, consisting essentially of directly compressing the pulverulent composition according to claim 9.

11. A tablet consisting essentially of the pulverulent composition as defined in claim 9, prepared in accordance with the process as defined in claim 10.

12. A tablet essentially free of granular starch, consisting essentially of: 30.0% to 100.0% of the non-spherical granules of microcrystalline mannitol of claim 1; greater than 0.1 to less than 0.8% of lubricant; 0% to 70.0% of ingredients other than mannitol and lubricant, wherein the percentages are expressed by dry weight, and their sum being equal to 100%.

13. A process of using a direct compression excipient, comprising providing the granules according to claim 1 and directly compressing the granules to form a tablet.

* * * * *